(12) United States Patent
Li et al.

(10) Patent No.: US 10,004,405 B2
(45) Date of Patent: Jun. 26, 2018

(54) SYSTEM AND IMAGING METHOD FOR USING PHOTOACOUSTIC EFFECT

(71) Applicant: NATIONAL TAIWAN UNIVERSITY, Taipei (TW)

(72) Inventors: Pai-Chi Li, Taipei (TW); Pei-Yu Chao, Taipei (TW); Kai-Wen Wu, Taipei (TW)

(73) Assignee: National Taiwan University, Taipei (TW)

( * ) Notice: Subject to any disclaimer, the term of this patent is extended or adjusted under 35 U.S.C. 154(b) by 44 days.

(21) Appl. No.: 14/721,096

(22) Filed: May 26, 2015

(65) Prior Publication Data
US 2016/0213256 A1 Jul. 28, 2016

(30) Foreign Application Priority Data
Jan. 22, 2015 (TW) .............................. 104102102 A

(51) Int. Cl.
*A61B 5/05* (2006.01)
*A61B 5/00* (2006.01)
(Continued)

(52) U.S. Cl.
CPC .......... *A61B 5/0095* (2013.01); *A61B 5/6848* (2013.01); *A61B 8/12* (2013.01); *A61B 8/4483* (2013.01); *G10K 15/046* (2013.01)

(58) Field of Classification Search
CPC ........ G10K 15/046; A61B 8/12; A61B 8/4483
See application file for complete search history.

(56) References Cited

U.S. PATENT DOCUMENTS 5,254,112 A * 10/1993 Sinofsky ............ A61B 5/02007
600/439
2005/0131289 A1 * 6/2005 Aharoni ............. A61B 5/02007
600/407
(Continued)

FOREIGN PATENT DOCUMENTS

TW 201119628 A 6/2011
TW 201227050 A 7/2012
(Continued)

OTHER PUBLICATIONS

Communication From the Taiwan Patent Office (A Taiwan Office Action With Objections to the Written Description for Containing Informalities) Regarding a Counterpart Taiwan Application Dated (Taiwan Year 105) dated Jan. 13, 2016.
(Continued)

*Primary Examiner* — Amelie R Gillman
(74) *Attorney, Agent, or Firm* — Rosenberg, Klein & Lee

(57) ABSTRACT

A system and an imaging method for using photoacoustic effect are provided in the present invention. The system includes a light source for generating a light beam, a wave-guide probe and an ultrasound receiving device. The wave-guide probe further has a reception portion and at least one transmission portion. The reception portion receives the light beam and then triggers a photoacoustic effect inside the reception portion so as thereby to generate at least one sound wave thereinside to be further transmitted to the at least one transmission portion. The transmission portion is merged into the organic medium. When the sound wave is transmitted to the transmission portion, an ultrasound area is generated inside the organic medium. The ultrasound receiving device is located adjacent to the organic medium, receives the ultrasound generated in the ultrasound area to form an
(Continued)

ultrasound image of the organic medium, so as to achieve the imaging method.

6 Claims, 10 Drawing Sheets

(51) Int. Cl.
  *G10K 15/04* (2006.01)
  *A61B 8/12* (2006.01)
  *A61B 8/00* (2006.01)

(56) References Cited

U.S. PATENT DOCUMENTS

| | | | |
|---|---|---|---|
| 2006/0229659 A1* | 10/2006 | Gifford | A61B 17/2202 606/200 |
| 2010/0174197 A1* | 7/2010 | Nakajima | A61B 5/0095 600/478 |
| 2011/0144496 A1 | 6/2011 | Li et al. | |
| 2012/0118042 A1 | 5/2012 | Gillis et al. | |
| 2012/0167694 A1 | 7/2012 | Li | |
| 2013/0085372 A1* | 4/2013 | Wada | A61B 5/0095 600/407 |
| 2014/0126323 A1 | 5/2014 | Li et al. | |

FOREIGN PATENT DOCUMENTS

| | | |
|---|---|---|
| TW | 201402075 A | 1/2014 |
| TW | 201419220 A | 5/2014 |
| TW | 201434411 A | 9/2014 |

OTHER PUBLICATIONS

Communication From the Taiwan Patent Office (A Taiwan Notice of Allowance) Regarding a Counterpart Taiwan Counterpart Taiwan Application Dated (Taiwan Year 105) dated Feb. 23, 2016.

* cited by examiner

SYSTEM AND IMAGING METHOD FOR USING PHOTOACOUSTIC EFFECT

This application benefit of Taiwan Patent Application Serial 104102102, filed Jan. 22, 2015, the subject matter of which is incorporated herein by reference.

BACKGROUND OF INVENTION

1. Field of the Invention

The invention relates to a system and a method for using photoacoustic effect, and more particularly to a system and an accompanying method that apply a portion of a wave-guide probe into an organic medium so as to perform imaging according to the photoacoustic effect.

2. Description of the Prior Art

Ultrasound imaging has been widely applied to medical diagnosis. Compared to other clinical medical imaging modalities such as X-ray, CT, MRI and nuclear imaging systems, ultrasound imaging is characterized as cost effective, free of ionizing radiation, non-invasive and real-time. It can also be portable, with sub-millimeter spatial resolution, and can be used for blood flow detection. Hence, ultrasound imaging has been widely utilized to assist clinical diagnosis.

Ultrasound imaging is based on reflection and backscattering. Specifically, a probe is required for radiating a sound wave into a human body. The interaction between sound wave and the tissues inside the human body produces echoes that are detected by the probe and images are reconstructed by the system based on the received echoes.

Recently, photoacoustic imaging has also emerged as a potentially useful imaging modality utilizing light and sound to make images based on the optical absorption properties of the image object. When an object is irradiated by light, some of the optical energy is absorbed followed by thermal expansion, and thus generating detectable sound waves. Therefore, an ultrasound probe can be used to detect such sound waves and reconstruct a photoacoustic image.

Despite the widespread use and potential clinical values, in some circumstances the ultrasound probes are too big, making the transmission of sound waves difficult, if not impossible It is clear that alternative methods to transmit sound waves are highly desirable.

SUMMARY OF THE INVENTION

In view of the current limitations in the size of the ultrasound probe which may lead to the problem of difficult access and failure to inspect small objects (e.g., cells and tissues), it is the primary objective of the present invention to provide a system and an imaging method that uses photoacoustic effects, where both operated by illuminating a wave-guide probe that is partially merged in an organic medium by a light beam. As the wave-guide probe absorbed the optical energy, sound wave are generated due to photoacoustic effect, and is transmitted into the organic medium, and thereby to perform the ultrasound imaging technique.

In the present invention, the system for using photoacoustic effect includes of a light source, a wave-guide probe and an ultrasound receiving device. The light source is to generate a light beam. The wave-guide probe has a reception portion and at least one transmission portion, in which the reception portion is to receive the light beam, and thereafter, a photoacoustic effect is triggered inside the reception portion of the wave-guide probe, where at least one sound wave is thereby generated inside the wave-guide probe. The sound wave generated inside the reception portion is then transmitted to the transmission portion. The transmission portion of the wave-guide probe is merged into the organic medium, which has the property of acoustic coupling. While the sound wave is transmitted to the transmission portion, a corresponding ultrasound area is generated inside the organic medium. The ultrasound imaging device located adjacent to the organic medium receives the ultrasound generated in the ultrasound area.

In one embodiment of the present invention, the light beam can be a laser beam, the wave-guide probe can be flexible, and the wave-guide probe can be made of metal or carbon fiber. Further, the wave-guide probe can have an internal transmission pathway that is wrapped by a metal for transmitting an agent to the ultrasound area. The agent can be one of a curative agent, a nutritive agent or a diagnostic agent. Further, a sample of cells in the ultrasound area of the organic medium can be extracted via the internal transmission pathway of the wave-guide probe, in which the organic medium can be a human body.

In one embodiment of the present invention, the wave-guide probe has the reception portion and a plurality of the transmission portions, in which the reception portion and the plurality of the transmission portions are separated by a distance. The transmission portions receive the sound wave and then generate a plurality of the ultrasound areas in the organic medium. The plurality of the ultrasound areas generates a plurality of the ultrasounds. The distances between the reception portion and the plurality of the transmission portions are adjustably, which can be designed to produce a focus point of the ultrasounds inside the organic medium. The wave-guide probe is wrapped by a plurality of sound-absorbed materials for forming the plurality of the transmission portions. The sound wave in the wave-guide probe is transmitted at a first sound wave velocity and is transmitted to the plurality of the transmission portions respectively at a plurality of first propagation times. The plurality of the ultrasounds in the organic medium are transmitted at a second sound wave velocity and are transmitted to the ultrasound receiving device respectively at a plurality of second propagation times. The ultrasound receiving device uses the first sound wave velocity, the second sound wave velocity and time lags between the plurality of the first propagation times and the respective plurality of the second propagation times to compute a spatial distribution of the plurality of the transmission portions.

In the present invention, the imaging method executed by aforesaid system includes a step of placing the transmission portion of the wave-guide probe into the organic medium; a step of triggering the light source to transmit the light beam to the reception portion of the wave-guide probe, so as to make the reception portion generate the sound wave and transmit the sound wave from the reception portion to the transmission portion, and further to generate the ultrasound area in the organic medium after the sound wave reaches the transmission portion; and a step of applying the ultrasound imaging device to receive the ultrasound generated in the ultrasound area so as thereby to form an ultrasound image inside the organic medium.

In the system and the method for using photoacoustic effect in accordance with the present invention, the wave-guide probe is utilized to apply the photoacoustic effect onto ultrasound imaging, thus the imaging recognition can be effectively enhanced. Also, by applying the wave-guide probe, smaller cells and tissues can be observed, therefore the aforesaid shortcomings of the art described in the background section can be effectively resolved.

In the system and the method for using photoacoustic effect in accordance with the present invention, the wave-guide probe is flexible, so the cells and tissues that are hard to be inspected in conventional setup, can now be clearly observed.

All these objects are achieved by the system and the method for using photoacoustic effect described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a system for using photoacoustic effect and an imaging method executed by using the system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
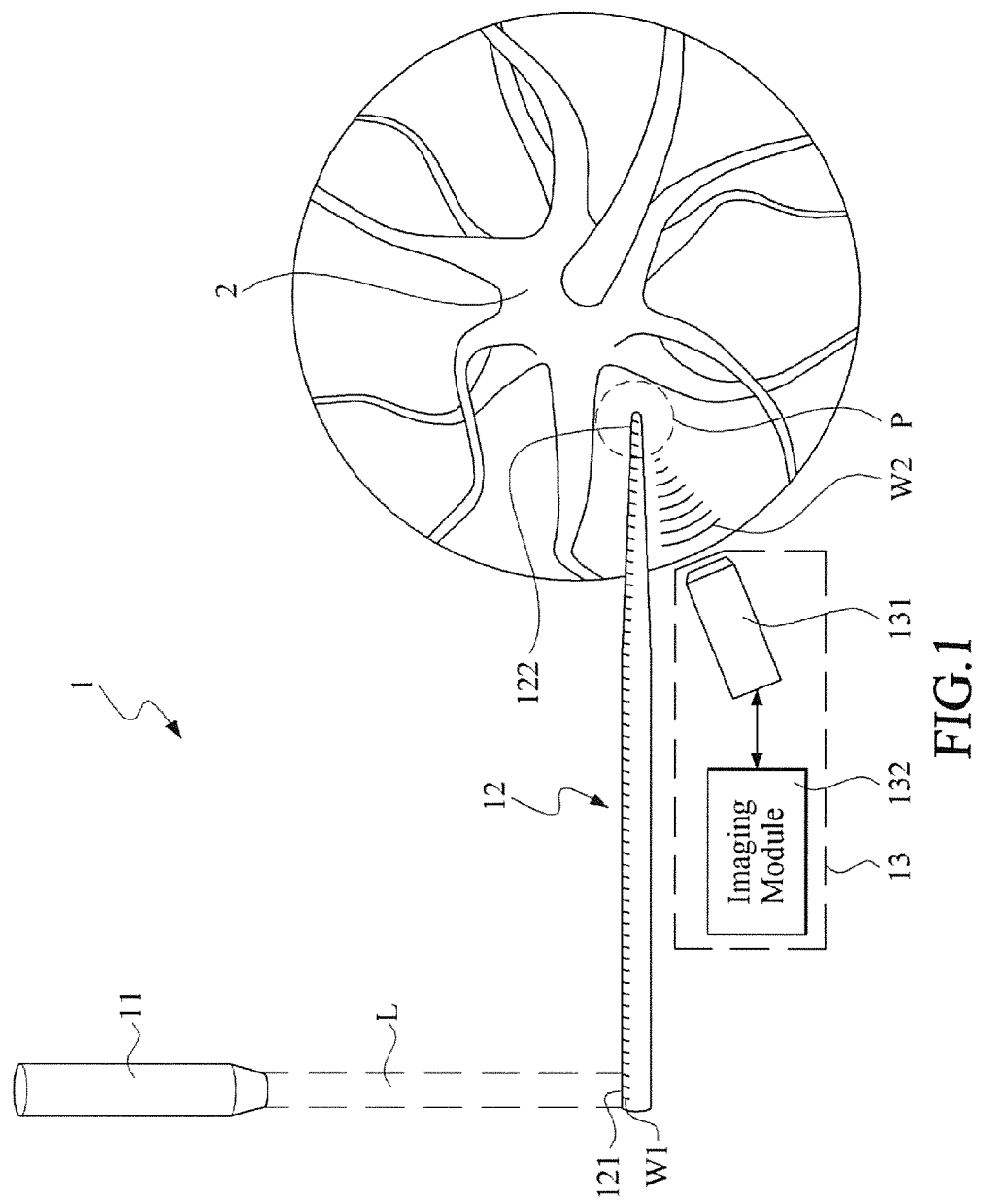
FIG. 1 is a schematic view of a first embodiment of the system for using photoacoustic effect in accordance with the present invention.

Referring now to FIG. 1, a schematic view of a first embodiment of the system for using photoacoustic effect in accordance with the present invention is shown. As illustrated, the first embodiment of the system 1 for using photoacoustic effect is applied to generate at least one ultrasound W2 inside an organic medium 2, such that an ultrasound image (not shown in the figure) for the corresponding portion of the organic medium 2 can be reconstructed, in which the organic medium 2 has the property of acoustic coupling. Herein, the meaning of acoustic coupling is that the matter is capable of transmitting a sound wave. In the present invention, the organic medium 2 can be, but not limited to, a human body. Further, the organic medium 2 can be a cell or tissue of a human body.

The system 1 for using photoacoustic effect of the present invention includes a light source 11, a wave-guide probe 12 and an ultrasound receiving device 13. The light source 11 can be a device to radiate a laser beam. Namely, the light source 11 can generate a light beam L, in which the light beam L is a laser beam. Preferably, the wavelength of the laser beam originated at the light source 11 can be adequately adjusted to meet practical needs.

The wave-guide probe 12 (formed as a wave guidance needle) has a reception portion 121 and a transmission portion 122, in which the reception portion 121 is located at one end of the wave-guide probe 12, the transmission portion 122 is merged into the organic medium 2. The transmission portion 122 can be referred to any portion of the wave-guide probe 12 that is not the reception portion 121. Preferably, the transmission portion 122 and the reception portion 121 are located at the opposite end of the wave-guide probe 12. Further, the wave-guide probe 12 can be a tube-shaped structure that can transmit the sound wave. In particular, the wave-guide probe 12 can be a needle and can be made of a material that can produce significant photoacoustic effect, such as a metal or a carbon fiber. Preferably, the wave-guide probe 12 is flexible.

The ultrasound receiving device 13 located adjacent to the organic medium 2 can include an ultrasound-receiving probe 131 and an imaging module 132, in which the imaging module 132 is electrically coupled with the ultrasound-receiving probe 131. Namely, the ultrasound receiving device 13 can be an imaging apparatus.

In the present invention, while in applying the system 1 for using photoacoustic effect, the transmission portion 122 of the wave-guide probe 12 is pierced into a portion to be inspected inside the organic medium 2, then the ultrasound-receiving probe 131 of the ultrasound imaging device 13 is moved close to the organic medium 2 (for example, a skin surface). The light source 11 is triggered to generate the light beam L and further to transmit the light beam L to the reception portion 121 of the wave-guide probe 12. Hence, a photoacoustic effect would occur at the reception portion 121 of the wave-guide probe 12, such that the reception portion 121 of the wave-guide probe 12 would generate at least one sound wave W1. The sound wave W1 generated at the reception portion 121 would be guided by the wave-guide probe 12 to reach the transmission portion 122. In the present invention, the sound wave W1 can be transmitted through the surface of the wave-guide probe 12. However, in some other embodiments, if the probe is solid, the sound wave W1 can also be transmitted through solid core of the wave-guide probe 12.

When the transmission portion 122 of the wave-guide probe 12 receives the sound wave W1, a corresponding ultrasound area P would be generated inside the organic medium 2, in which the ultrasound area P would perform as a source to radiate at least one ultrasound W2. The ultrasound W2 would be transmitted onto the surface of the organic medium 2 so as to make the ultrasound-receiving probe 131 of the ultrasound receiving device 13 receive the ultrasound W2 generated in the ultrasound area P. The ultrasound W2 is forwarded to the imaging module 132 in a signal manner, such that the imaging module 132 can utilize the ultrasound W2 to form an ultrasound image. Particularly, the imaging technique is already mature in the art, and thus details there-about would be omitted herein.

Figure 2:
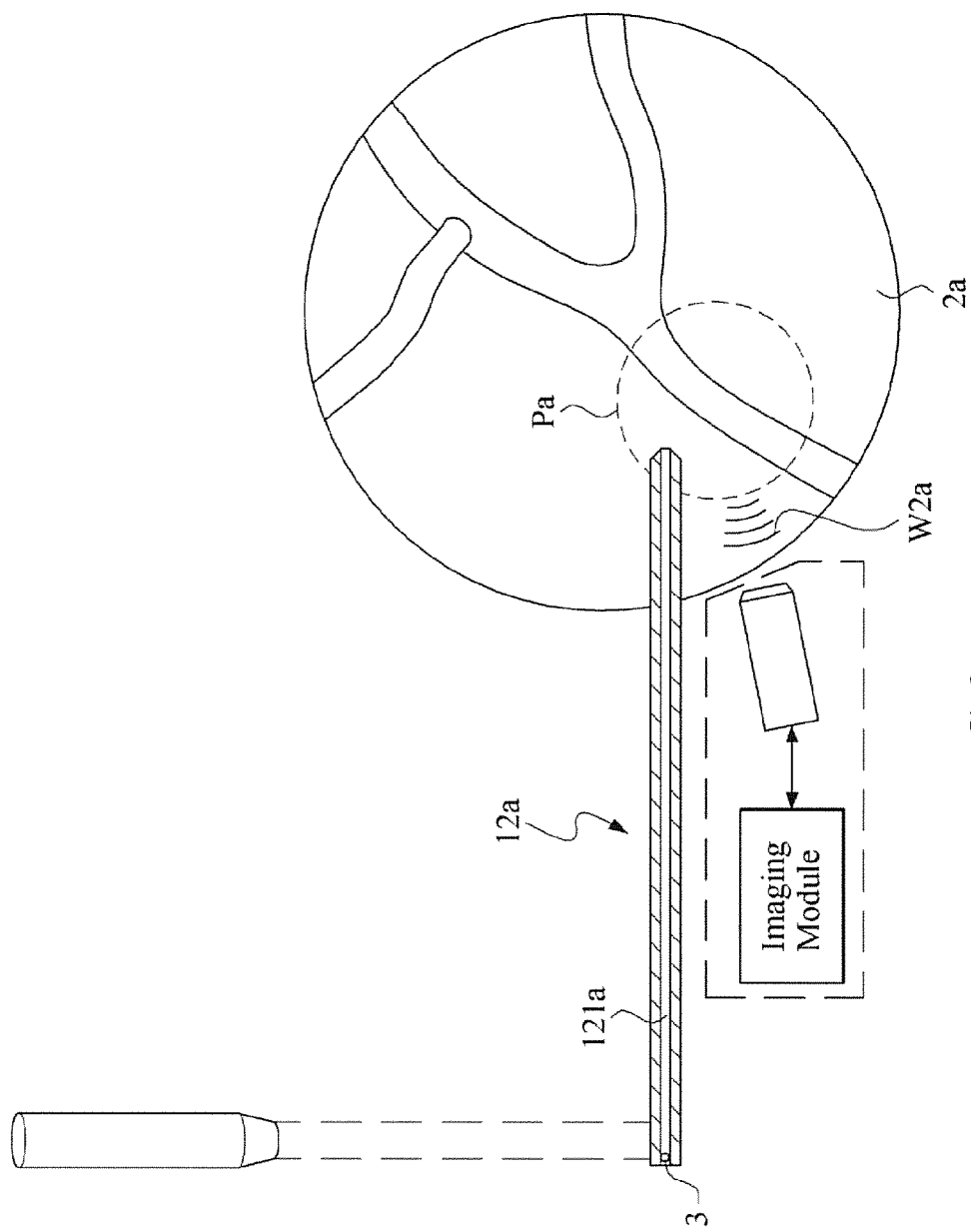
FIG. 2 is a schematic view of a second embodiment of the system for using photoacoustic effect in accordance with the present invention.

Referring now to FIG. 2, a schematic view of a second embodiment of the system for using photoacoustic effect in accordance with the present invention is shown. As illustrated, compared with the first embodiment of FIG. 1, the major change in the second embodiment of the system for using photoacoustic effect is that the wave-guide probe 12a includes an internal transmission pathway 121a wrapped or coated by a metal for conveying an agent 3 to the ultrasound area P, in which the agent 3 can be a curative agent, a nutritive agent, a diagnostic agent or any the like. In particular, the curative agent can be a therapy medicine, the nutritive agent can be a healthcare product, and the diagnostic agent can be a staining agent. The internal transmission pathway 121a of the wave-guide probe 12a is used to sample cells of the organic medium 2a in the ultrasound area Pa. Further, in the second embodiment, the wave-guide probe 12a has an internal transmission pathway 121a, therefore it can serve both the therapy and the sampling purposes. While the wave-guide probe 12a serves the therapy purpose, some medicines conveyed through the internal transmission pathway 121a may be strengthened by the ultrasound W2a, or the ultrasound W2a may be used to break the shell or the exterior coating of the medicine. While the wave-guide probe 12a serves the sampling purpose, the internal transmission pathway 121a may be used to observe the state of the organic medium 2a, such as the therapy result, the damage, or the size of a tumor. Meanwhile, all other details of the second embodiment are the same as those of the first embodiment, and thus would be omitted herein.

Figure 3:
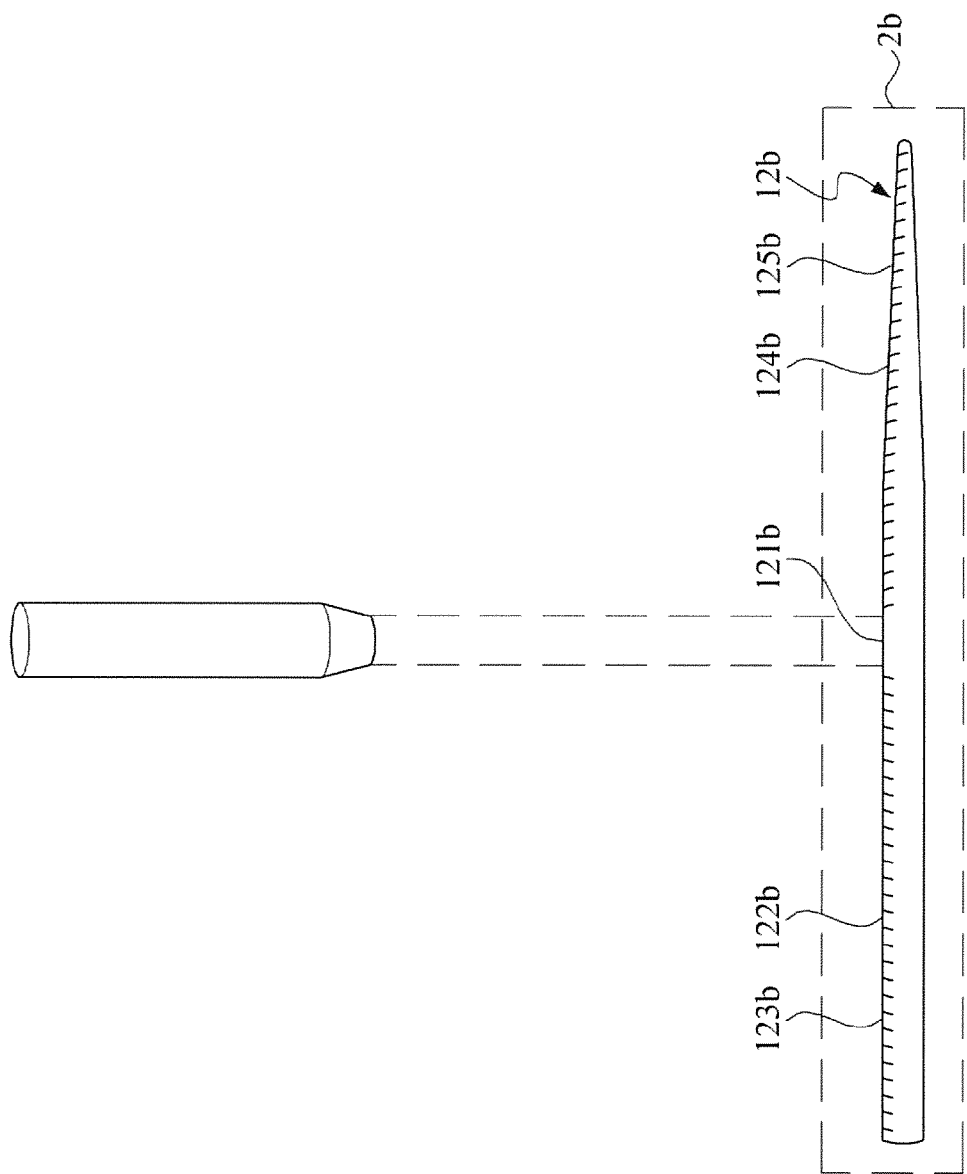
FIG. 3 is a schematic view of a third embodiment of the system for using photoacoustic effect in accordance with the present invention.

Referring now to FIG. 3, a schematic view of a third embodiment of the system for using photoacoustic effect in accordance with the present invention is shown. As illustrated, compared with the first embodiment of FIG. 1, the major change in the third embodiment of the system for using photoacoustic effect is that the wave-guide probe 12b has a reception portion 121b and four transmission portions 122b, 123b, 124b and 125b, so that the organic medium 2b would have a plurality of the ultrasound areas (not shown in the figure).

Figure 4:
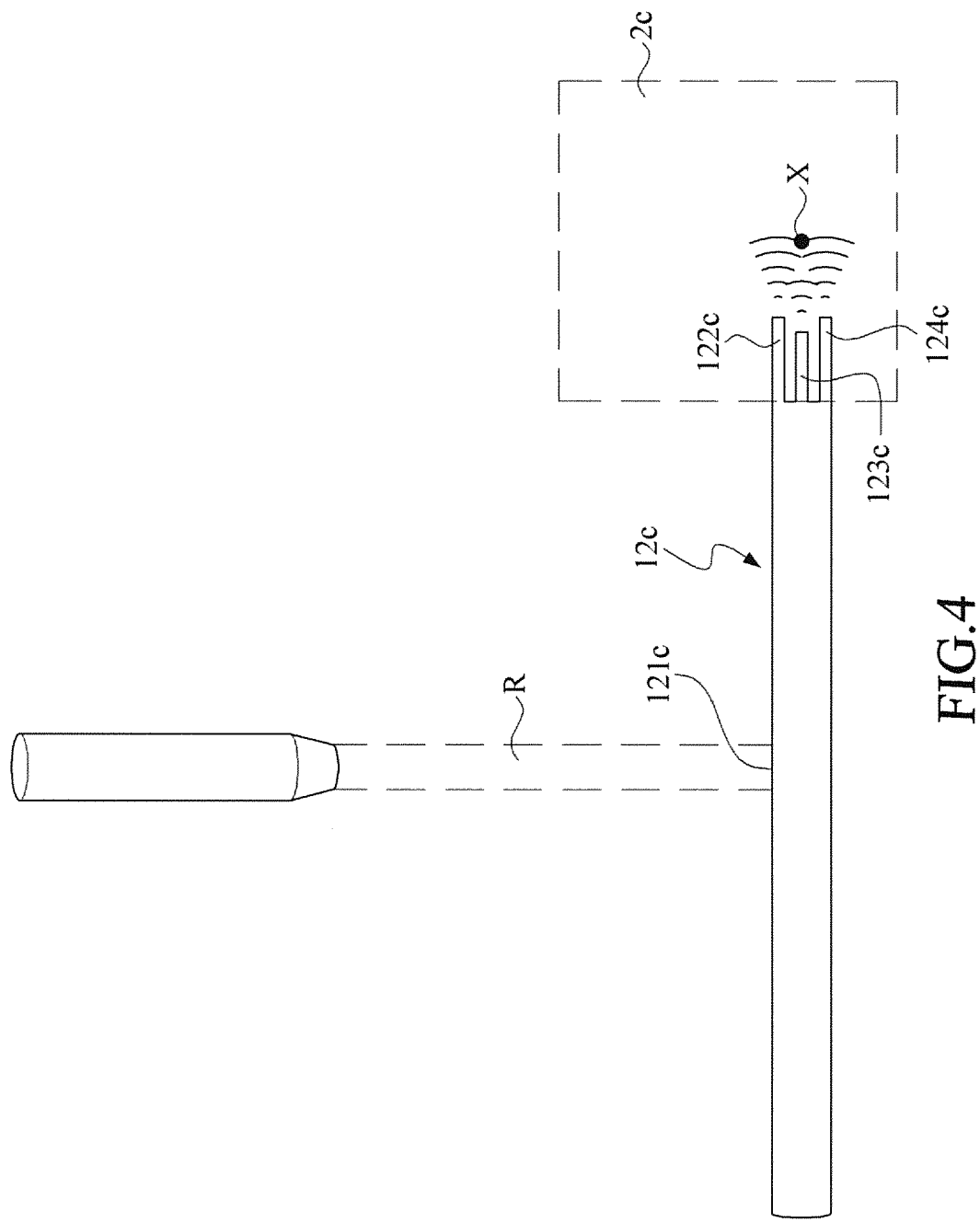
FIG. 4 is a schematic view of a fourth embodiment of the system for using photoacoustic effect in accordance with the present invention.

Referring now to FIG. 4, a schematic view of a fourth embodiment of the system for using photoacoustic effect in accordance with the present invention is shown. As illustrated, compared with the first embodiment of FIG. 1, the major change in the fourth embodiment of the system for using photoacoustic effect is that, at one end of the wave-guide probe 12c, a plurality of protrusions (three, 122c, 123c, 124c) is included to perform as the transmission portions 122c, 123c, 124c. After the reception portion 121c of the wave-guide probe 12c receives the light beam R, corresponding sound waves (not shown in the figure) would be transmitted to the respective transmission portions 122c, 123c, 124c. According to different locations of the transmission portions 122c, 123c, 124c, different timings for the corresponding sound waves to arrive the respective transmission portions 122c, 123c, 124c are expected. In practice, by varying the lengths of the transmission portions 122c, 123c, 124c, the travel distances between the reception portion 121c and the respective transmission portions 122c, 123c, 124c, or the individual lengths of the transmission portions 122c, 123c, 124c themselves, the timing for the ultrasounds to arrive at the transmission portions 122c, 123c, 124c would be different. Upon such an arrangement, the ultrasounds would be adjustable to be focused in the focus point. For example, as shown in FIG. 4, the focus point in this fourth embodiment would fall at the focus point X inside the organic medium 2c. The ultrasound radiated from the ultrasound area corresponding to the focus point X would contribute to a better imaging quality.

Figure 5:
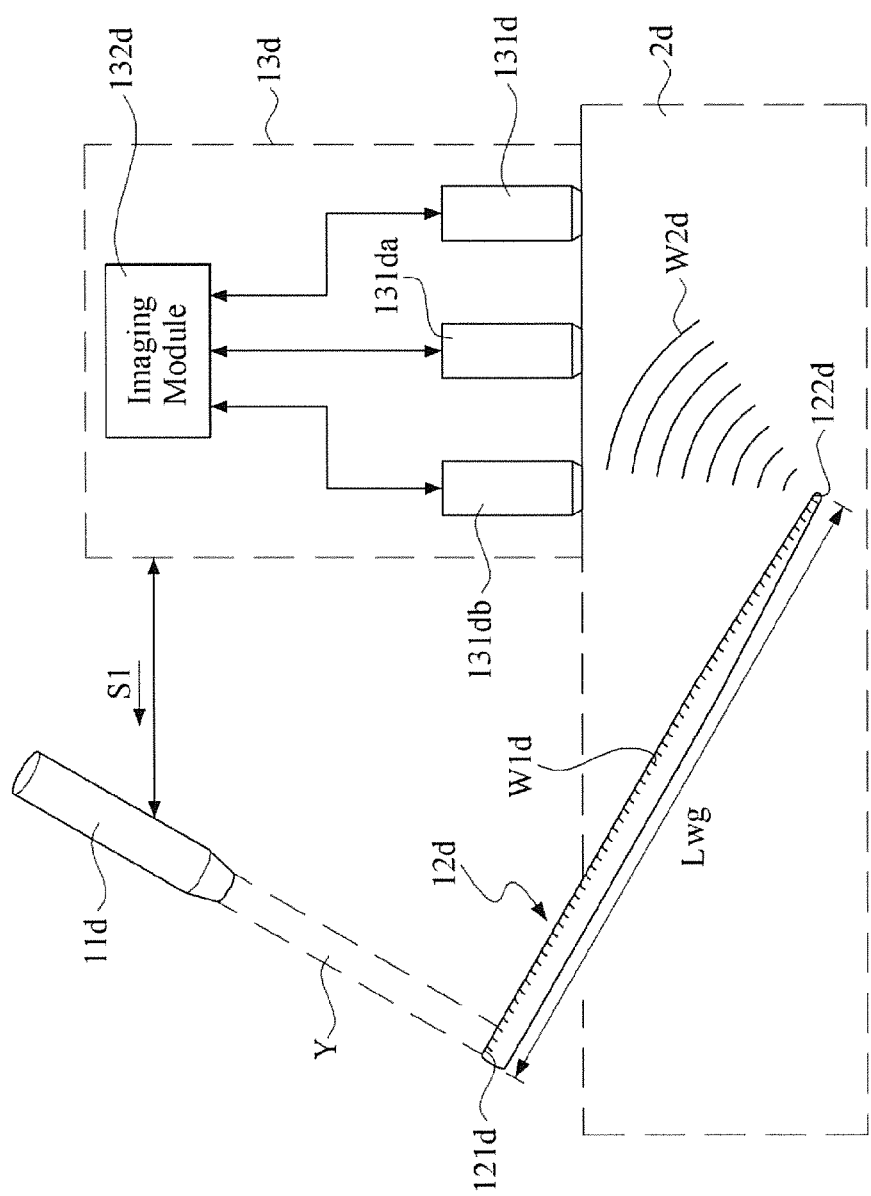
FIG. 5 is a schematic view of a fifth embodiment of the system for using photoacoustic effect in accordance with the present invention.

Referring now to FIG. 5, a schematic view of a fifth embodiment of the system for using photoacoustic effect in accordance with the present invention is shown. As illustrated, compared with the first embodiment of FIG. 1, the major change in the fifth embodiment of the system for using photoacoustic effect is that this fifth embodiment includes at least three ultrasound-receiving probes 131d, 131da, 131db.

In an operation, the ultrasound receiving device 13d would issue a trigger signal S1 to the light source 11d (preferably, through the imaging module 132d). At the same time, the ultrasound receiving device 13d would trigger the ultrasound-receiving probe 131d to pose at a signal-receiving mode. In the signal-receiving mode, the ultrasound-receiving probe 131d of the ultrasound receiving device 13d would begin to receive and record the incoming signals and the corresponding times. Also, as soon as the light source 11d receives the trigger signal S1, a light beam Y would be directly or indirectly (through a optical fiber, for example) transmitted to the reception portion 121d of the wave-guide probe 12d. After the reception portion 121d absorbs the light beam Y, the photoacoustic effect would be turned on to generate at least one sound wave W1d, and the sound wave W1d would go through the wave-guide probe 12d to reach the transmission portion 122d. Then, the ultrasound W2d generated at the transmission portion 122d would go through the organic medium 2d and thus be received and recorded by the ultrasound-receiving probe 131d of the ultrasound receiving device 13.

In the present invention, a fixed distance Lwg is defined between the reception portion 121d and the transmission portion 122d of the wave-guide probe 12d, and a Cwg (the velocity of the fastest sound wave transmitted in the wave guide probe) is defined as the velocity of the sound wave W1d transmitted in the wave-guide probe 12d. The sound wave velocity Cwg would be varied according to different materials for the wave-guide probe 12d. Therefore, when changing for the material of the wave-guide probe 12d, the sound wave velocity shall be calibrated as well. In addition, a C0 (second sound wave velocity) is defined as the velocity of the sound wave transmitted in the organic medium 2d. This velocity C0 also requires to be calibrated in advance so as to ensure the following computation of the ultrasound-radiating position (i.e. the position of the transmission portion 122d, or the position of the ultrasound area in other embodiment). After the calibration of the sound wave velocities Cwg, C0 of the wave-guide probe 12d and the organic medium 2d respectively is done, the time of flight (defined as tf) is the travel time of the sound wave from the reception portion 121d to the receiving device 131d. Further, through integrating the calibrated sound wave velocities of the wave-guide probe 12d and the organic medium 2d, the distance between the ultrasound-radiating position (i.e. the position of the transmission portion 122d, or the position of the ultrasound area in other embodiment) and the position of the ultrasound-receiving probe 131d (defined as L0) can be calculated by applying the equation of tf=Lwg/Cwg+L0/C0. In the aforesaid calculation, only a single distance between the position of the ultrasound-receiving probe 131d and the ultrasound-radiating position (i.e. the position of the transmission portion 122d, or the position of the ultrasound area in other embodiment) is obtained. Similarly, the other distances (defined as L1 and L2) related respectively to the ultrasound-receiving probes 131da, 131db can also be obtained by applying the aforesaid equation. Further, by applying the triangulation location, the ultrasound-radiating position can be obtained.

The aforesaid triangulation location includes the following equations:

$$(x-x_0)^2+(y-y_0)^2+(z-z_0)^2=L_0^2.$$

$$(x-x_1)^2+(y-y_1)^2+(z-z_1)^2=L_1^2.$$

$$(x-x_2)^2+(y-y_2)^2+(z-z_2)^2=L_2^2.$$

The aforesaid $x_0$, $x_1$, $x_2$, $y_0$, $y_1$, $y_2$, $z_0$, $z_1$, $z_2$ are 3D coordinates of the ultrasound-receiving probes 131d, 131da, 131db. Thereby, the intersection point can then be calculated and then to derive the ultrasound-radiating position.

Figure 6:
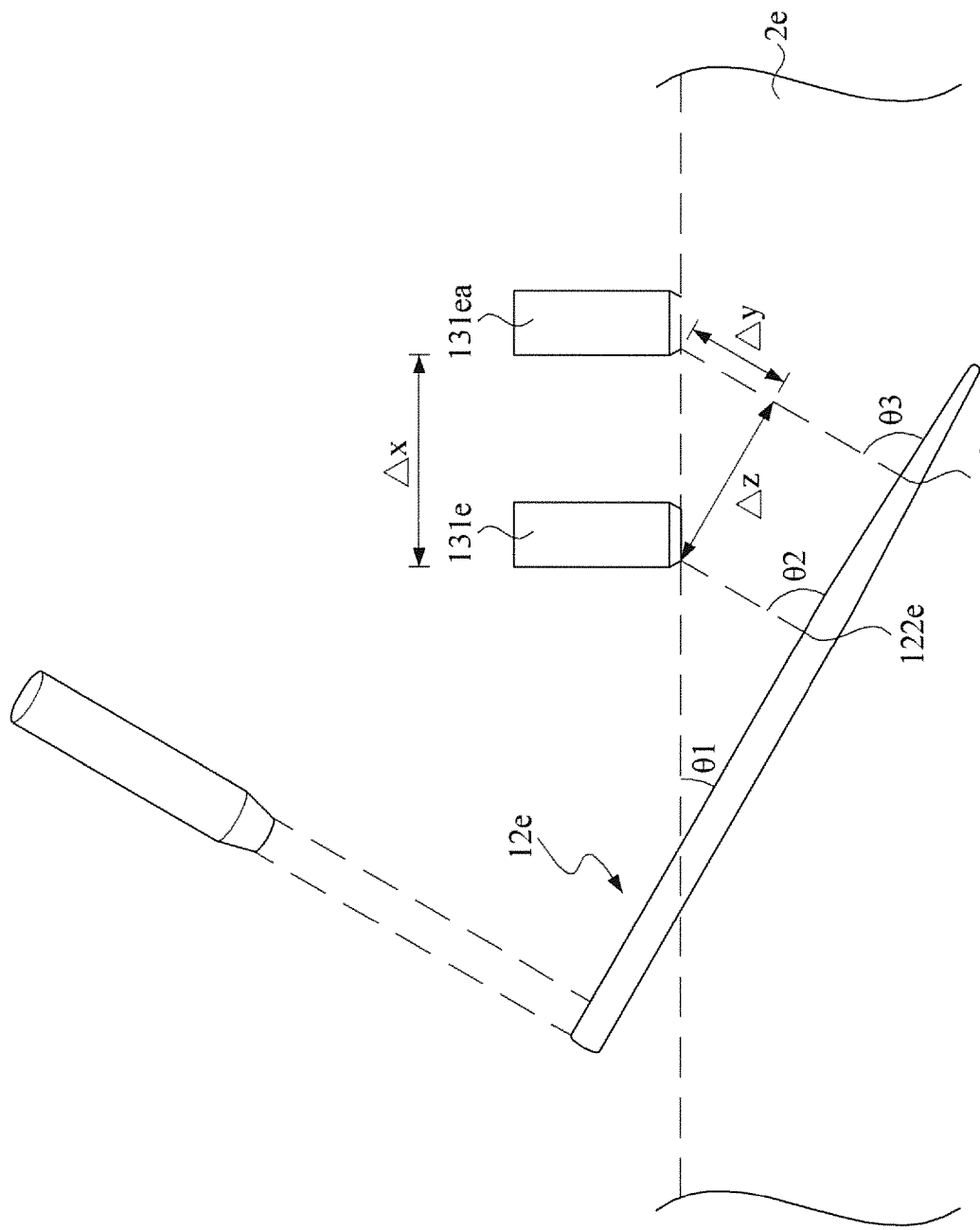
FIG. 6 is a schematic view of a sixth embodiment of the system for using photoacoustic effect in accordance with the present invention.
Figure 7:
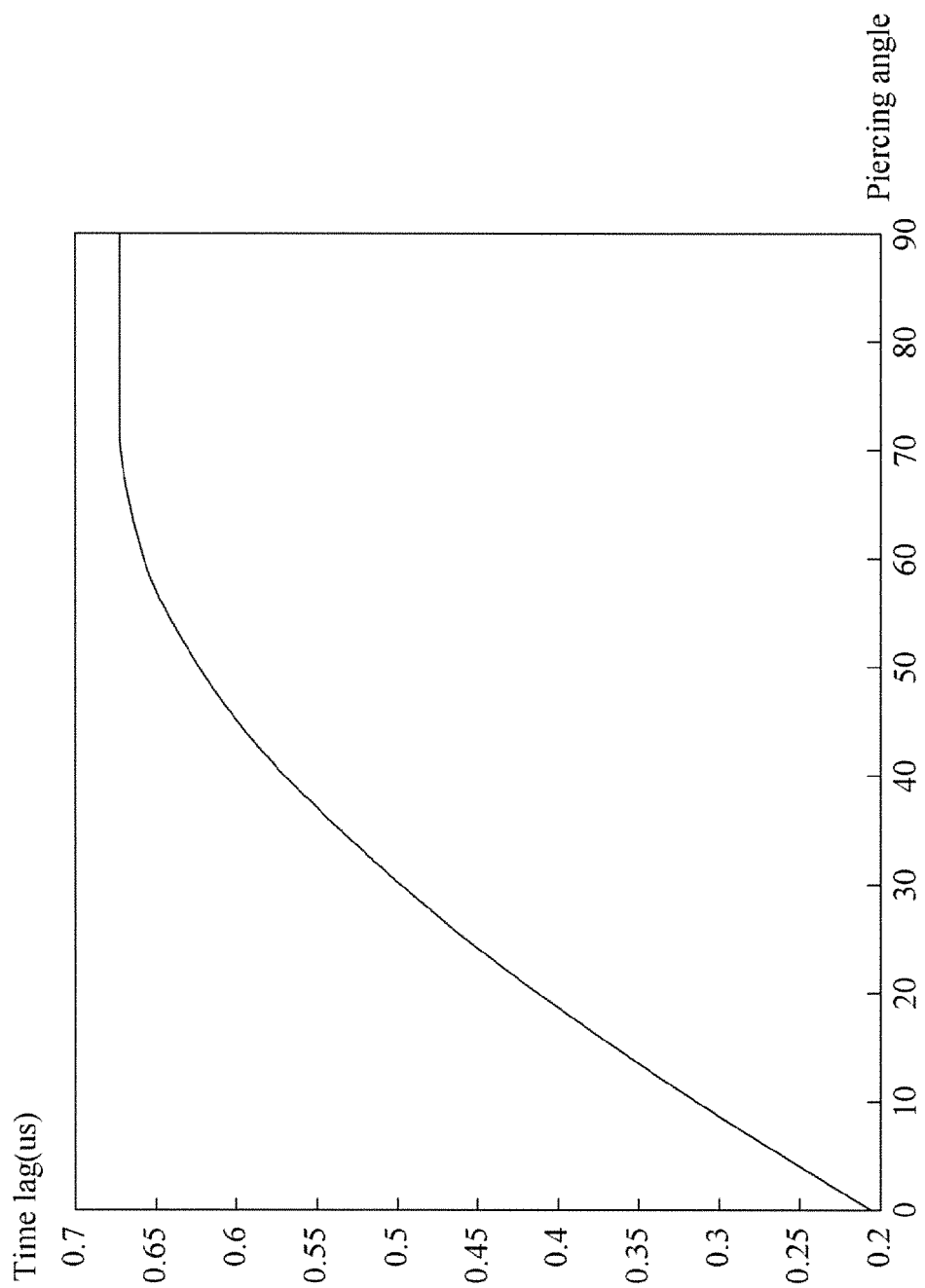
FIG. 7 is a diagram showing a relationship between the time lag and the piercing angle in accordance with the present invention.

Refer now to both FIG. 6 and FIG. 7, in which FIG. 6 is a schematic view of a sixth embodiment of the system for using photoacoustic effect in accordance with the present invention, and FIG. 7 is a diagram showing a relationship between the time lag and the piercing angle in accordance with the present invention. As shown, compared with the first embodiment of FIG. 1, the major change in the sixth embodiment of the system for using photoacoustic effect is that the wave-guide probe 12e is to pierce the organic medium 2e by a piercing angle θ1. The wave-guide probe 12e made of a specific material may have various ultrasound-radiating positions (as the transmission portions 122e, 122f shown in FIG. 6), or all the wave-guide probe 12e can be the ultrasound-radiating position. Since the same ultrasound-receiving probes 131e, 131ea can be applied to receive the signals from different ultrasound-radiating positions at different times, so the analytic method for this embodiment would be slightly different to that of the aforesaid embodiment with a single ultrasound-radiating position.

In general, the wave-guide probe 12e is a linear probe having a piercing angle θ1 according to the operation angle piercing the organic medium 2e. If the ultrasound-receiving probes 131e, 131ea were parallel to the wave-guide probe 12e, then, through various probe positions, the signals received firstly at times would keep a linear relationship. Namely, the first signals received by different ultrasound-receiving probes 131e, 131ea are transmitted from different radiating positions (transmission portions 122e, 122f) of the wave-guide probe 12e but with the same angle. Practically, as shown, the ultrasound transmitted from the transmission portion 122e would be forwarded to the ultrasound-receiving probe 131e by a transmission angle θ2, and the ultrasound transmitted from the transmission portion 122f would be forwarded to the ultrasound-receiving probe 131ea by a transmission angle θ3, in which the transmission angle θ2 and the transmission angle θ3 are equal.

Hence, in order to control the positions of the ultrasound-receiving probes 131e and 131ea by fixing a controlled distance Δx and allowing differential distances Δy, Δz, the time lag corresponding to different piercing angles θ1 can be calculated by computer simulations according to the calibrated sound velocities of the wave-guide probe 12e and the organic medium 2e. As shown in FIG. 7, if Δx=1 mm, the time lag Δt=t1−t2 indicates the time lag for the two transmission portions 122e and 122f to transmit the ultrasounds respectively to the ultrasound-receiving probes 131e and 131e. Thus, the wave-guide probe piercing angle (θ1) can be directly referred by mapping the time lag (t1−t2).

In the present invention, the aforesaid computer simulation can be performed by computing the following equation.

$$\Delta t = t1-t2 = \Delta z/Cwg + \Delta y/C0 = (z1-z2)/Ceg + (y1-y2)/C0.$$

In the aforesaid equation, z1, z2, y1 and y2 are coordinates of the ultrasound-receiving probes 131e and 131e.

In the aforesaid example, all the wave-guide probe can be the candidate radiating positions by wrapped with the material capable of absorbing the sound wave so as to control the sound wave to leave only from some predetermined positions. Namely, the ultrasound-radiating positions and the number thereof can be controlled by purposely wrapping with the sound-absorbed material. Refer now to both FIG. 8 and FIG. 9, in which FIG. 8 is a schematic view of a seventh embodiment of the system for using photoacoustic effect in accordance with the present invention, and FIG. 9 shows a spatial feasible region of the wave-guide probe in accordance with the present invention.

Figure 8:
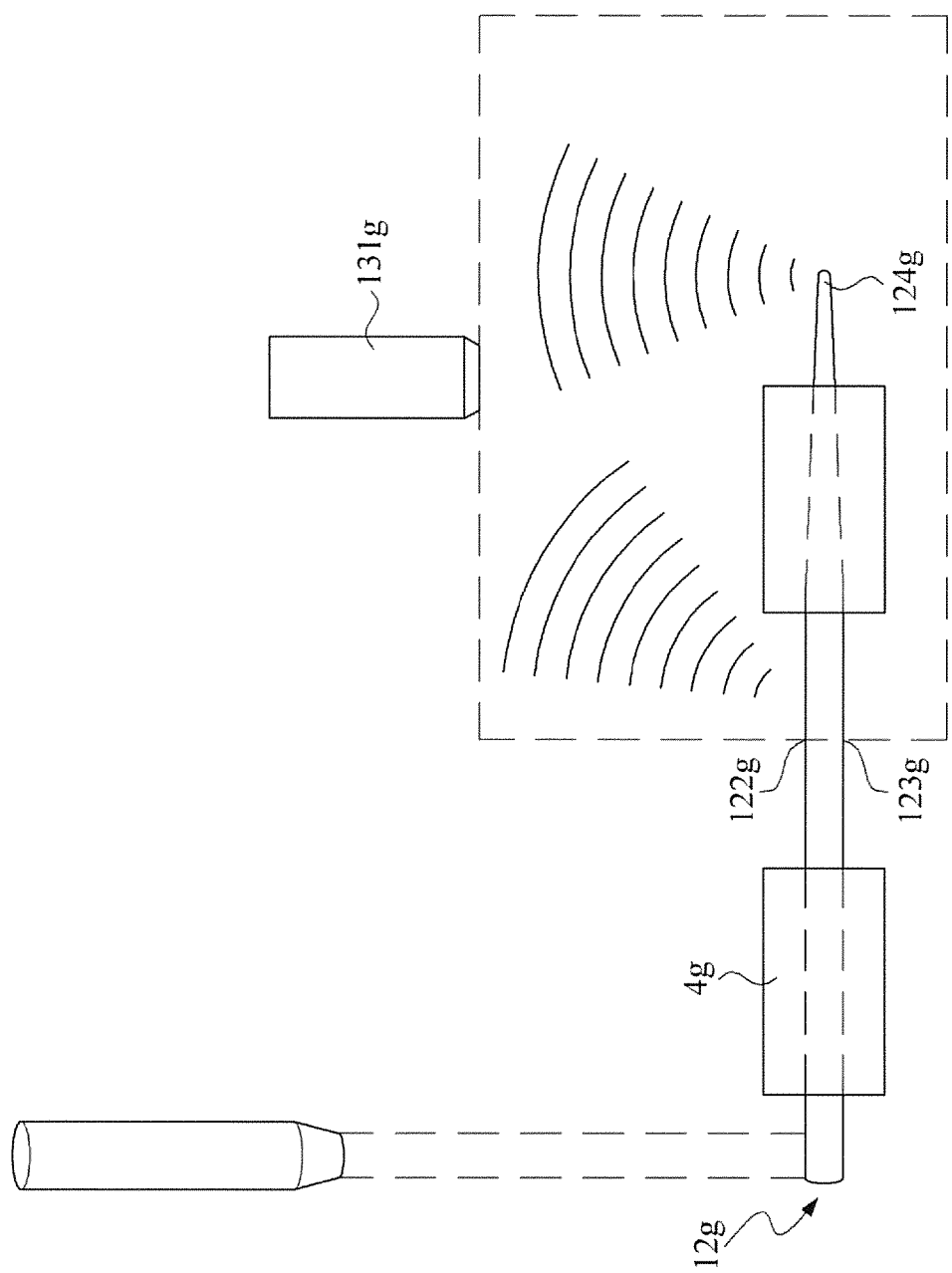
FIG. 8 is a schematic view of a seventh embodiment of the system for using photoacoustic effect in accordance with the present invention.
Figure 9:
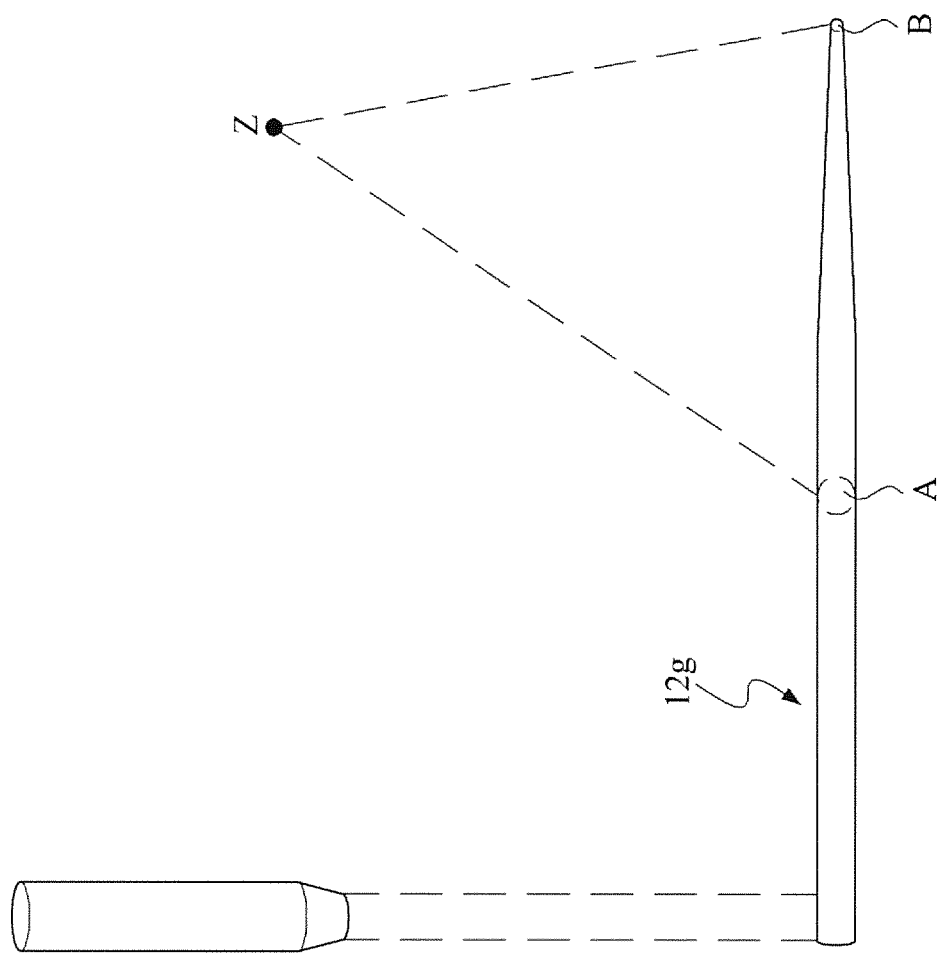
FIG. 9 shows a spatial feasible region of the wave-guide probe in accordance with the present invention.

As shown in FIG. 8, compared with the first embodiment of FIG. 1, the major change in the seventh embodiment of the system for using photoacoustic effect is that a plurality of sound-absorbed materials 4g are wrapped or coated around the wave-guide probe 12g so as to allow three transmission portions 122g, 123g and 124g. In this embodiment, the sound-radiating positions can be calculated. By adopting the equation for the embodiments shown in FIG. 5 and FIG. 6, the time for the sound wave to reach different ultrasound-radiating positions (transmission portion 122g, 123g and 124g) and the receiving time of the ultrasound-receiving probe 131g can be used to compute the respective ultrasound-radiating positions (transmission portion 122g, 123g and 124g).

Further, by applying the computed ultrasound-radiating positions (transmission portion 122g, 123g and 124g) to match the corresponding distribution of the ultrasound-radiating position (transmission portion 122g, 123g and 124g) at the wave-guide probe 12g, then the spatial distribution relationship for the whole wave-guide probe 12g can be obtained. As shown in FIG. 9, the probe position Z represents for the position of the ultrasound-receiving probe 131g, area A represents for the positions of the transmission portion 122g, 123g, and area B represents for the position of the transmission portion 124g.

Figure 10:
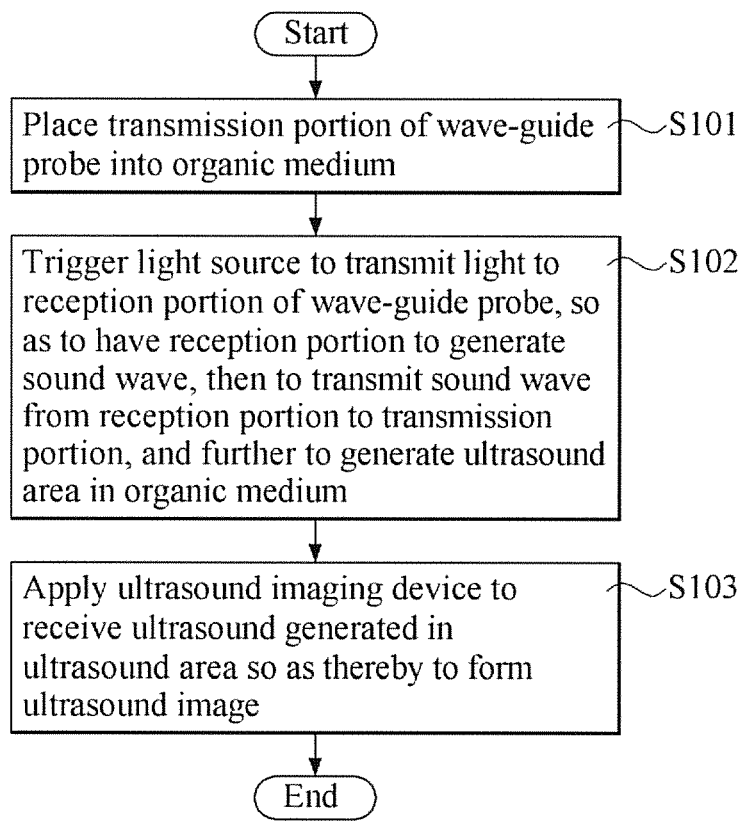
FIG. 10 is a flowchart of the preferred imaging method executed by using the system for using photoacoustic effect in accordance with the present invention.

Referring now to FIG. 10, a flowchart of the preferred method for the system for using photoacoustic effect in accordance with the present invention is shown. As listed in FIG. 10 (by referring to FIG. 1), the imaging method is executed by using the abovementioned system 1, and includes the following steps.

Step S101: The transmission portion 122 of the wave-guide probe 12 is placed into the organic medium 2.

Step S102: The light source 11 is triggered (i.e. energized to action) to transmit a light beam L to the reception portion 121 of the wave-guide probe 12, such that the reception portion 121 can generate a corresponding sound wave W1, and the sound wave W1 generated at the reception portion 121 is then transmitted to the transmission portion 122. As soon as the sound wave W1 reaches the transmission portion 122, a corresponding ultrasound area P is generated inside the organic medium 2.

Step S103: The ultrasound receiving device 13 is applied to receive the ultrasound W2 generated in the ultrasound area P, and then the ultrasound W2 can be utilized to process the ultrasound image of the organic medium 2.

In summary, by providing the system for using photoacoustic effect in accordance with the present invention, since the wave-guide probe is applied to integrate the photoacoustic effect and the ultrasound imaging so as to transmit a light beam to a portion of the wave-guide probe merged in the organic medium and further to trigger the photoacoustic effect inside the wave-guide probe to generate a corresponding sound wave to be transmitted into the organic medium for performing the ultrasound imaging, thus the imaging recognition can be effectively enhanced. Also, after the wave-guide probe is adapted, even smaller cells and tissues can be observed, so that the aforesaid shortcomings in this art described in the background section can be effectively resolved. Further, since the wave-guide probe is flexible, so the cells and tissues, hard to be inspected before, can now be clearly observed.

While the present invention has been particularly shown and described with reference to a preferred embodiment, it will be understood by those skilled in the art that various changes in form and detail may be without departing from the spirit and scope of the present invention.

What is claimed is:

1. A system for using a photoacoustic effect to generate at least one ultrasound wave within an organic medium capable of acoustic coupling, the system comprising:
    a light source for generating a light beam;
    a longitudinally extended wave-guide probe consisting essentially of a material that generates the photoacoustic effect responsive to impingement by the light beam to thereby produce at least one sound wave, the wave-guide probe having:
        a reception portion configured to be disposed external to the organic medium, the reception portion being impinged by the light beam to produce the at least one sound wave by the photoacoustic effect within the wave-guide probe at the reception portion; and
        at least one transmission portion extended from the reception portion and configured to be at least partially disposed within the organic medium, the wave-guide probe thereby providing a unitary structure that both generates and transmits the at least one sound wave, wherein the at least one sound wave is propagated longitudinally from the reception portion to the at least one transmission portion to generate at least one ultrasound area inside the organic medium, to thereby produce at least one ultrasound wave in the at least one ultrasound area; and
    an ultrasound receiver configured to be located adjacent to the organic medium to receive the at least one ultrasound wave.

2. The system for using a photoacoustic effect of claim 1, wherein the light beam is a laser beam.

3. The system for using a photoacoustic effect of claim 1, wherein the wave-guide probe is flexible.

4. The system for using photoacoustic effect of claim 1, wherein the material is metal and wherein the wave-guide probe further has an internal transmission pathway, and the internal transmission pathway is a through bore extending through the metal wave-guide probe for transmitting an agent to the at least one ultrasound area, and the agent is one of a curative agent, a nutritive agent and a diagnostic agent.

5. The system for using a photoacoustic effect of claim 1, wherein the at least one transmission portion comprises a plurality of transmission portions, the at least one ultrasound area comprises a plurality of ultrasound areas, the at least one ultrasound wave comprises a plurality of ultrasound waves, and a distance between the reception portion and each of the plurality of transmission portions is adjustably set to produce a focus point of the plurality of ultrasound waves inside the organic medium.

6. An imaging method comprising:
    providing a light source for generating a light beam;
    providing a longitudinally extended wave-guide probe consisting essentially of a material that generates a photoacoustic effect responsive to impingement by the light beam to thereby produce at least one sound wave, the wave-guide probe having a reception portion and at least one transmission portion spaced from the reception portion to define a unitary structure that both generates and transmits the at least one sound wave;
    positioning the at least one transmission portion of the wave-guide probe at least partially within an organic medium, and the reception portion of the wave-guide probe being disposed external to the organic medium;
    triggering the light source to transmit the light beam to impinge upon the reception portion of the wave-guide probe to produce the at least one sound wave by the photoacoustic effect within the wave-guide probe at the reception portion, and propagating the at least one sound wave longitudinally from the reception portion to the at least one transmission portion, and transmitting the at least one sound wave from the at least one transmission portion to generate at least one ultrasound area inside the organic medium to thereby produce at least one ultrasound wave in the at least one ultrasound area; and
    applying an ultrasound receiver to receive the at least one ultrasound wave and forming an ultrasound image of the at least one ultrasound area.

* * * * *